United States Patent [19]

Smith, III

[11] Patent Number: 5,857,989
[45] Date of Patent: Jan. 12, 1999

[54] DYNAMIC ORTHOPEDIC KNEE BRACE ASSEMBLY

[76] Inventor: Kirby Smith, III, 3636 Blakeford Way, Marietta, Ga. 30062

[21] Appl. No.: 977,094

[22] Filed: Nov. 24, 1997

[51] Int. Cl.[6] .................................................... A61F 5/00
[52] U.S. Cl. ............................................. 602/26; 602/16
[58] Field of Search .................................. 602/5, 16, 20, 602/23, 26

[56] References Cited

U.S. PATENT DOCUMENTS

| | | |
|---|---|---|
| 3,387,305 | 6/1968 | Shafer . |
| 3,581,741 | 6/1971 | Rosman . |
| 4,240,414 | 12/1980 | Theisler . |
| 4,554,913 | 11/1985 | Womack et al. ........................ 602/16 |
| 4,751,920 | 6/1988 | Mauldin et al. . |
| 4,781,180 | 11/1988 | Solomonow . |
| 4,805,606 | 2/1989 | McDavid, III . |
| 4,854,308 | 8/1989 | Drillo ..................................... 602/16 |
| 4,955,369 | 9/1990 | Bledsoe et al. ......................... 602/16 |
| 4,961,416 | 10/1990 | Moore et al. . |
| 4,991,571 | 2/1991 | Kausek .................................... 602/16 |
| 5,052,379 | 10/1991 | Airy et al. .............................. 602/16 |
| 5,063,916 | 11/1991 | France et al. ...................... 602/16 X |
| 5,117,814 | 6/1992 | Luttrell et al. . |
| 5,135,469 | 8/1992 | Castillo ................................... 602/16 |
| 5,213,094 | 5/1993 | Bonutti ............................. 602/16 X |
| 5,277,698 | 1/1994 | Taylor . |
| 5,383,845 | 1/1995 | Nebolon ............................ 602/16 X |
| 5,433,699 | 7/1995 | Smith, III . |
| 5,512,039 | 4/1996 | White . |
| 5,624,389 | 4/1997 | Zepf . |
| 5,662,595 | 9/1997 | Chesher et al. . |

OTHER PUBLICATIONS

Advertisement for the Innovation C.Ti Brace.
Advertisement for the Innovation C.Ti. [2] Brace.
Advertisement for the Innovation C.Ti. [2], C. Ti. [2] Lite, Edge, Edge Lite, Sentry C180 and MVP Braces.
Advertisement for the Innovation Sentry Brace.
Advertisement for the Innovation MVP Brace.
Advertisement for the Brace Technologies Cincinnati ACL Brace.
Advertisement for the Omni Scientific OS–5™ Brace.
Advertisement for the 3M Health Care Lennox Hill™ Brace.
Advertisement for the Orthotic Consultants SKO™ Brace.
Advertisement for the Orthotic Consultants TKO™ Brace.
Advertisement for the Townsend Design ACL Brace.
Advertisement for the Smith & Nephew Donjoy DONJOY 4–Point™ Brace.
Advertisement for the Smith & Nephew Donjoy GOLD-POINT™ Brace.
Advertisement for the Smith & Nephew Donjoy PLAY-MAKER™ Brace.
Advertisement for the Smith & Nephew Donjoy DEFI-ANCE ™ Brace.
Advertisement for the Generation Orthotics Poli–Axial Osteoarthritis Brace.
Advertisement for the Orthomedics ECKO™ II Brace.

*Primary Examiner*—Linda C. M. Dvorak
*Attorney, Agent, or Firm*—Caesar, Rivise, Bernstein, Cohen & Pokotilow, Ltd.

[57] ABSTRACT

A knee brace assembly for various uses, e.g., restricting anterior tibial movement. The knee brace assembly includes a proximal cuff for engaging the wearer's leg above the knee and a distal cuff for engaging the wearer's leg below the knee. The proximal and distal cuffs are linked together by a hinge that permits pivotal movement of the proximal cuff relative to the distal cuff. The proximal cuff has lateral and medial portions each having a slot extending there along. A strap guiding assembly is slidably mounted within each of the slots. Each strap guiding assembly is arranged to slide between a proximal extreme when the wearer's leg is in flexion and a distal extreme as the wearer extends his or her leg. A biasing device biases each strap guiding assembly towards its proximal extreme. A cross-strap, having free ends and a length, is provided for engagement with the wearer's leg. The cross-strap attaches to the wearer's leg below the knee and wraps behind the knee in crisscross fashion. The free ends of the strap attach to the strap guiding assembly. The cross-strap is operative in response to extension of the wearer's leg to pull the strap guiding assembly from the proximal extreme towards the distal extreme thus creating a force counteractive to abnormal anterior movement of the tibia.

21 Claims, 11 Drawing Sheets

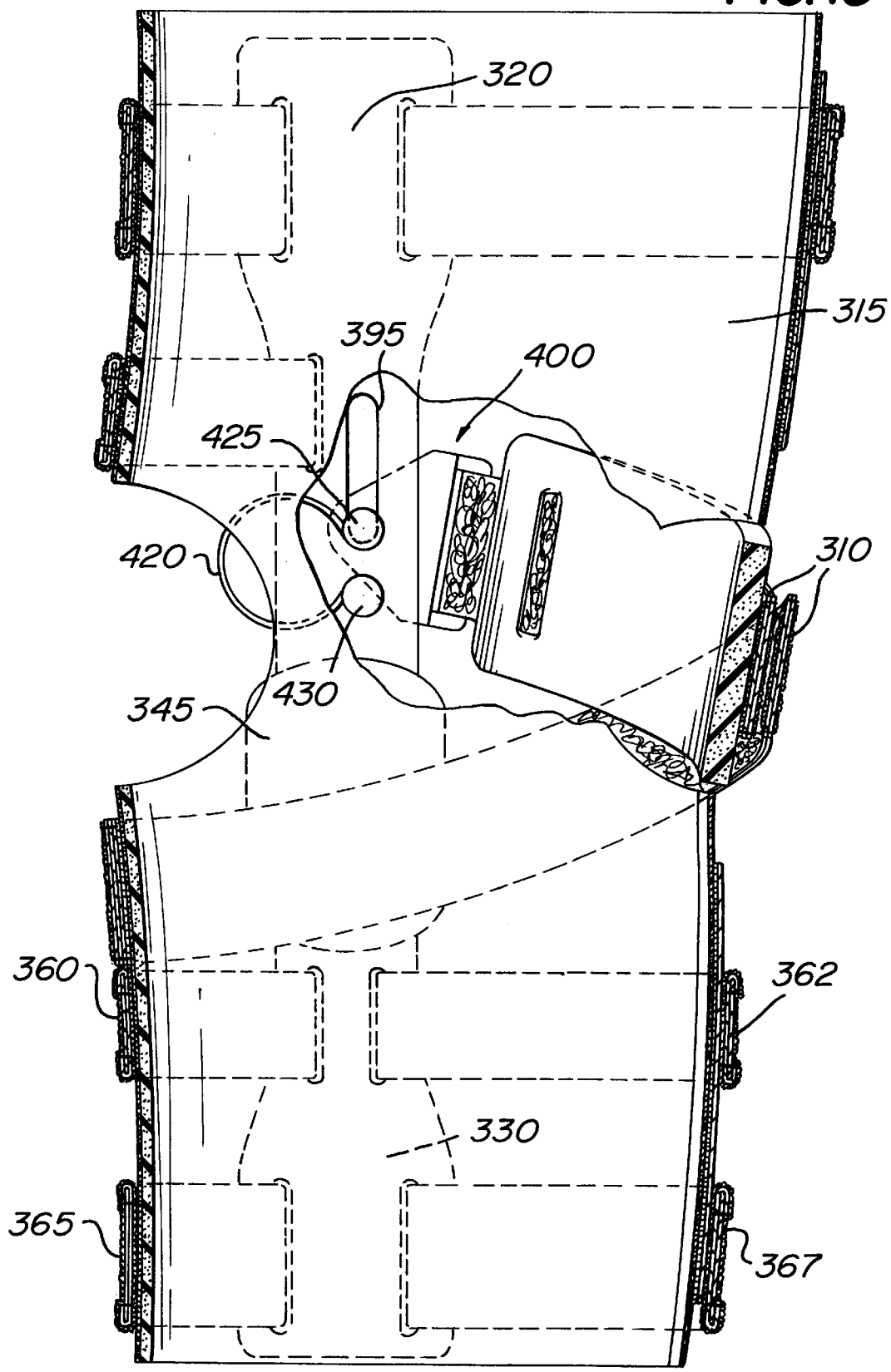

DYNAMIC ORTHOPEDIC KNEE BRACE ASSEMBLY

This invention relates generally to orthopedic knee braces, and more particularly to knee braces for use by persons having anterior cruciate ligament laxity or insufficiency to protect them from injury due to abnormal anterior tibial movement.

BACKGROUND OF THE INVENTION

Various types of knee braces are shown in the patent literature and are commercially available. The following constitute examples of prior art braces that deal with restricting anterior movement of the tibia: U.S. Pat. Nos. 4,9055,369 (Bledsoe et al.); 5,433,699 (Smith, III); 4,751,920 (Mauldin et al.) and 4,781,180 (Solomonow). The apparatus shown by Mauldin is a knee brace that has a first attachment portion to attach the brace to the wearer's thigh and a second attachment portion to attach the brace to the wearer's tibia and a hinge connected to the medial side of the first and second attachment portions by way of a thigh bar and tibia bar, respectively. An adjustable gearing mechanism located at the hinge permits the wearer to limit the amount of rotation of the tibia bar with respect to the thigh bar. However, this brace suffers from failing to be able to prevent anterior translation of the tibia by the application of posterior pressure directed at the tibia tubercle location. Instead, like its predecessors, the Mauldin apparatus attempts to limit tibial rotation by limiting medial hinge motion.

The apparatus shown by Solomonow is a knee brace having an upper framework attached to the thigh and a lower framework attached to the lower leg just below the knee. These two frameworks are hinged on the medial and lateral sides of the leg (bilateral hinge). A bell crank is pivotally connected to the lower framework. An adjustable screw coupled to one side of the bell crank engages an offset portion of the upper framework whenever the leg is extended. The other side of the bell crank is coupled to a tibial restraining strap. As the leg is extended, the lower framework and bell crank are rotated counterclockwise until the offset of the upper framework contacts the screw, rotating the bell crank in a clockwise direction and thereby tightening the tibial restraining strap against anterior movement of the tibia.

The apparatus shown by Bledsoe et al. is a knee brace which also utilizes bilateral hinges to connect the thigh support and calf support sections. The bilateral hinges basically comprise adjustable drive plates that alternate the pivoting point of the thigh support and calf support throughout leg flexion and extension. By varying the pivot point at different points throughout leg extension, a counter shearing force is generated to reduce the shearing force created by the quadriceps muscle which cause the undesirable anterior shift of the tibia of the leg.

Other prior art knee braces are disclosed in U.S. Pat. Nos. 3,581,741 (Rosman); 5,277,698 (Taylor); 5,512,039 (White); 3,387,305 (Shafer); 4,240,414 (Theisler); 4,805,606 (McDavid, III); 4,961,416 (Moore et al.); and U.S. Pat. No. 4,854,308 (Drillio).

Examples of prior art knee braces which are commercially available are: Innovative Sports C.Ti., C.Ti.$^2$, C.Ti.$^2$ Lite, Edge, Edge Lite, Sentry, C180 and MVP all of which are sold by Innovation Sports, Inc. Of Irvine, Calif.; Cincinnati ACL which is sold by Brace Technologies, Inc. Of Cincinnati, Ohio, the OS-5 (TM) non-custom functional knee support which is sold by Omni Scientific, Inc. Of Martinez, Calif.; the Lennox Hill (TM) OTS Brace and Spectralite Brace which are sold by 3M Health Care of Long Island City, N.Y.; the SKO (TM) and TKO (TM) knee orthoses which are manufactured by Orthotic Consultants of Southern California; the ACL model knee brace which is sold by Townsend Design of Bakersfield, Calif.; the DON-JOY 4-Point (TM), Gold-Point (TM), Playmaker (TM), and Defiance (TM) all of which are sold by Smith & Nephew Donjoy, Inc. of Carlsbad, Calif; the Poli-Axial Osteoarthritis Brace which is sold by Generation Orthotics, Inc.; and, the ECKO (TM) II Extension Control Knee Orthosis which is sold by Orthomedics of Brea, Calif.

While the aforementioned patents seem suitable for their intended purposes, it would be a significant advance in the art to provide a knee brace assembly that applies posterior pressure on the wearer's tibia in response to extension of the wearer's leg through the use of a cross-strap that is positioned over the wearer's tibia, wrapped in crisscross manner behind the wearer's knee and attached to biased strap guides slidably mounted to the brace assembly.

OBJECTS OF THE INVENTION

Accordingly, it is a general object of this invention to provide a knee brace assembly which overcomes the disadvantages of the prior art.

It is a further object of this invention to provide a knee brace assembly for restricting anterior movement of the wearer's tibia.

It is a further object of this invention to provide a knee brace assembly for restricting abnormal anterior tibial movement without preventing the wearer from being able to fully extend his/her leg.

It is a further object of this invention to provide a knee brace assembly that is inexpensive to manufacture.

It is a further object of this invention to provide a knee brace assembly that is reliable in operation.

It is a further object of this invention to provide a knee brace assembly that is simple in construction.

It is a further object of this invention to provide a knee brace assembly that is lightweight.

It is a further object of this invention to provide a knee brace assembly that is comfortable when worn.

SUMMARY OF THE INVENTION

These and other objects of this invention are achieved by providing a knee brace assembly for restricting anterior tibial movement. The knee brace assembly includes a proximal cuff for engaging the wearer's leg above the knee and a distal cuff for engaging the wearer's leg below the knee. The proximal and distal cuffs are linked together by a hinge means that permits pivotal rotation of the proximal cuff relative to the distal cuff. The proximal cuff has lateral and medial portions each having a slot extending there along. A strap guiding means is slidably mounted within each of the slots. Each strap guiding means is arranged to slide between a proximal extreme when the wearer's leg is in flexion and a distal extreme as the wearer extends his or her leg. A biasing means biases each strap guiding means towards its proximal extreme. A cross-strap, having free ends and a length, is provided for engagement with the wearer's leg. The cross-strap attaches to the wearer's leg below the knee and wraps behind the knee in crisscross fashion. The free ends of the strap attach to the strap guiding means. The cross-strap is operative in response to extension of the wearer's leg to pull the strap guiding means from the proximal extreme towards the distal extreme thus creating a force counteractive to abnormal anterior movement of the tibia.

DESCRIPTION OF THE DRAWINGS

Other objects and many attendant features of this invention will become readily appreciated as the same becomes better understood by reference to the following detailed description when considered in connection with the accompanying drawings wherein:

FIG. 13 is a sectional view taken along line 13—13 of FIG. 8; and, FIG. 14 is an exploded isometric view of a second embodiment of the present invention.

DETAILED DESCRIPTION OF THE PREFERRED EMBODIMENTS

Figure 1:
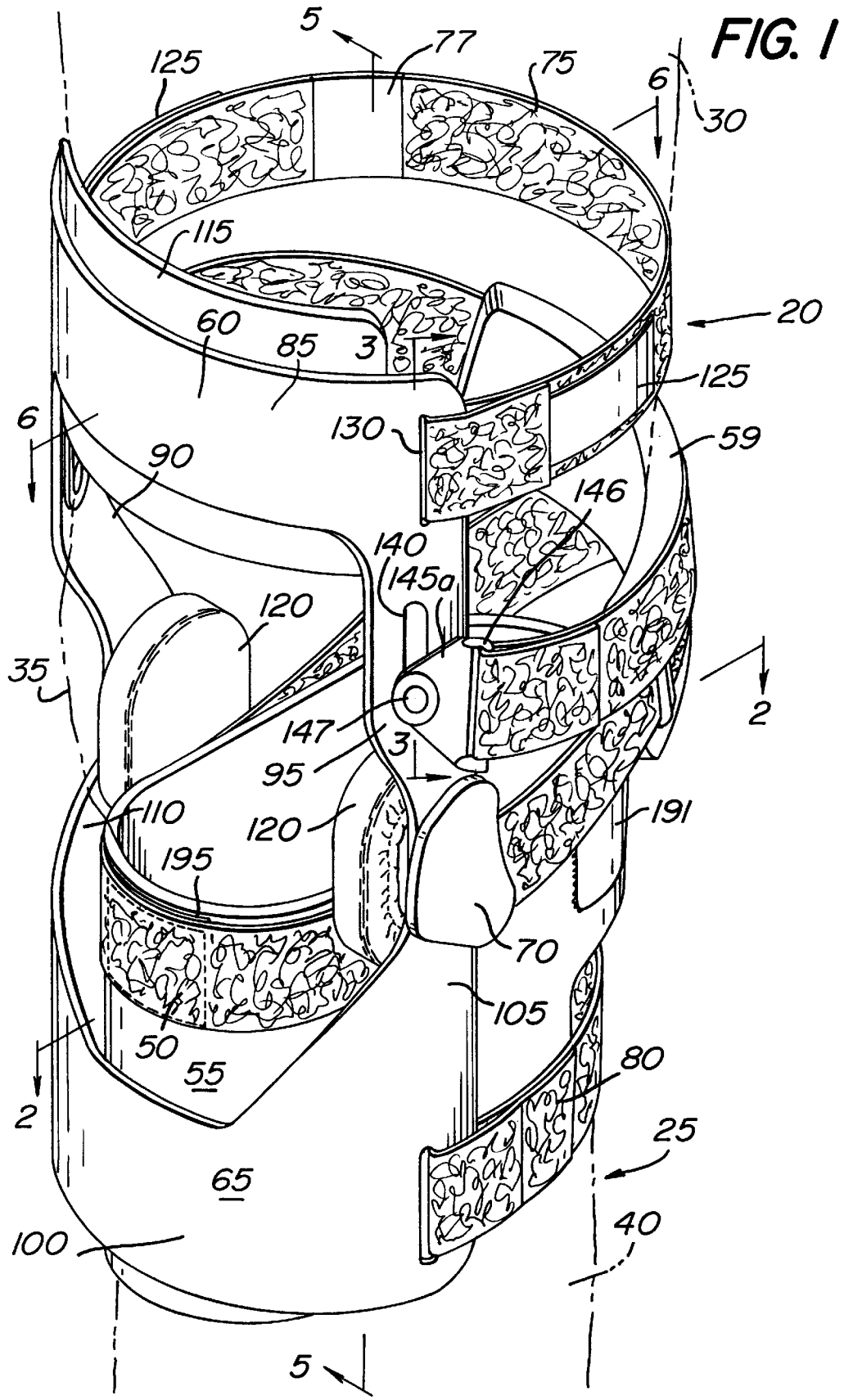
FIG. 1 is an isometric view of a first embodiment of the present invention.
Figure 3:
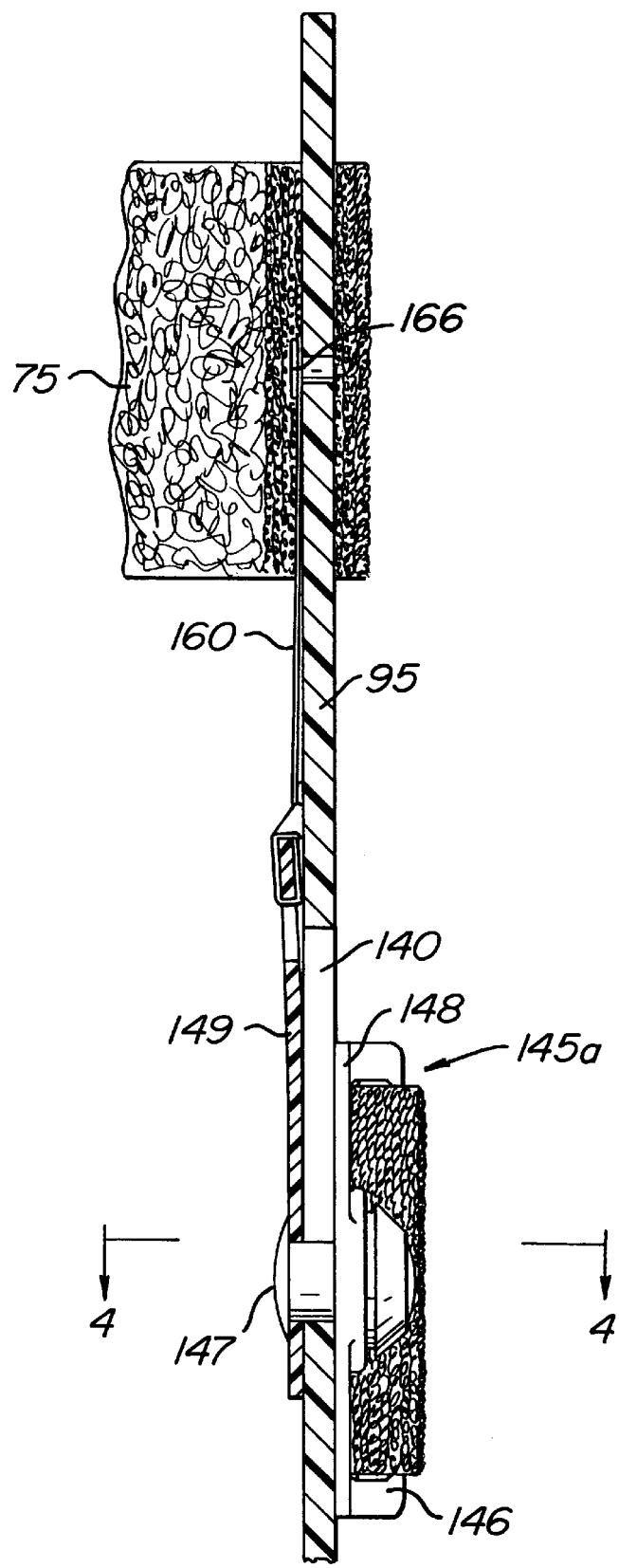
FIG. 3 is an enlarged sectional view taken along line 3—3 of FIG. 1.
Figure 5:
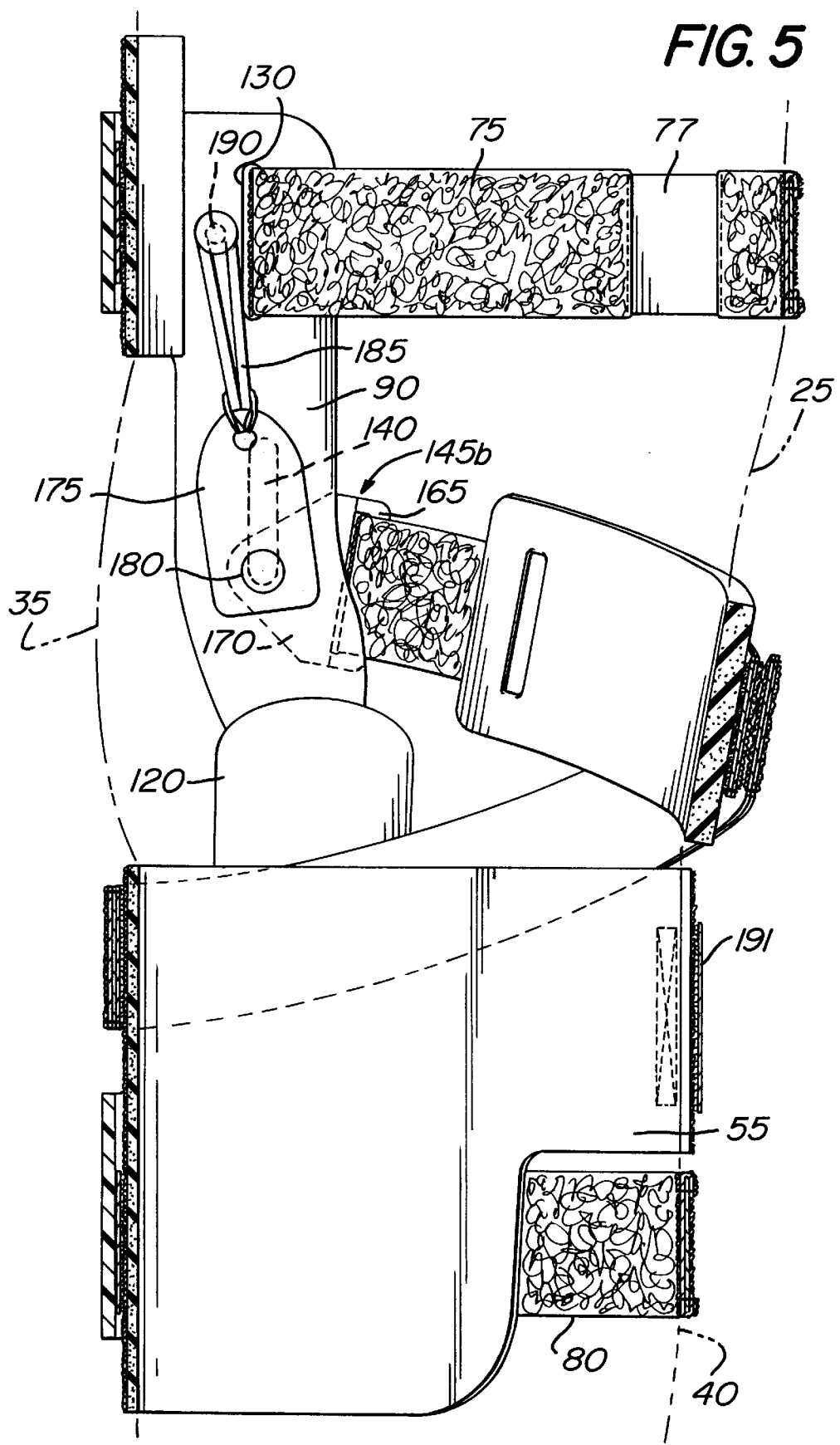
FIG. 5 is a sectional view taken along line 5—5 of FIG. 1.
Figure 7:
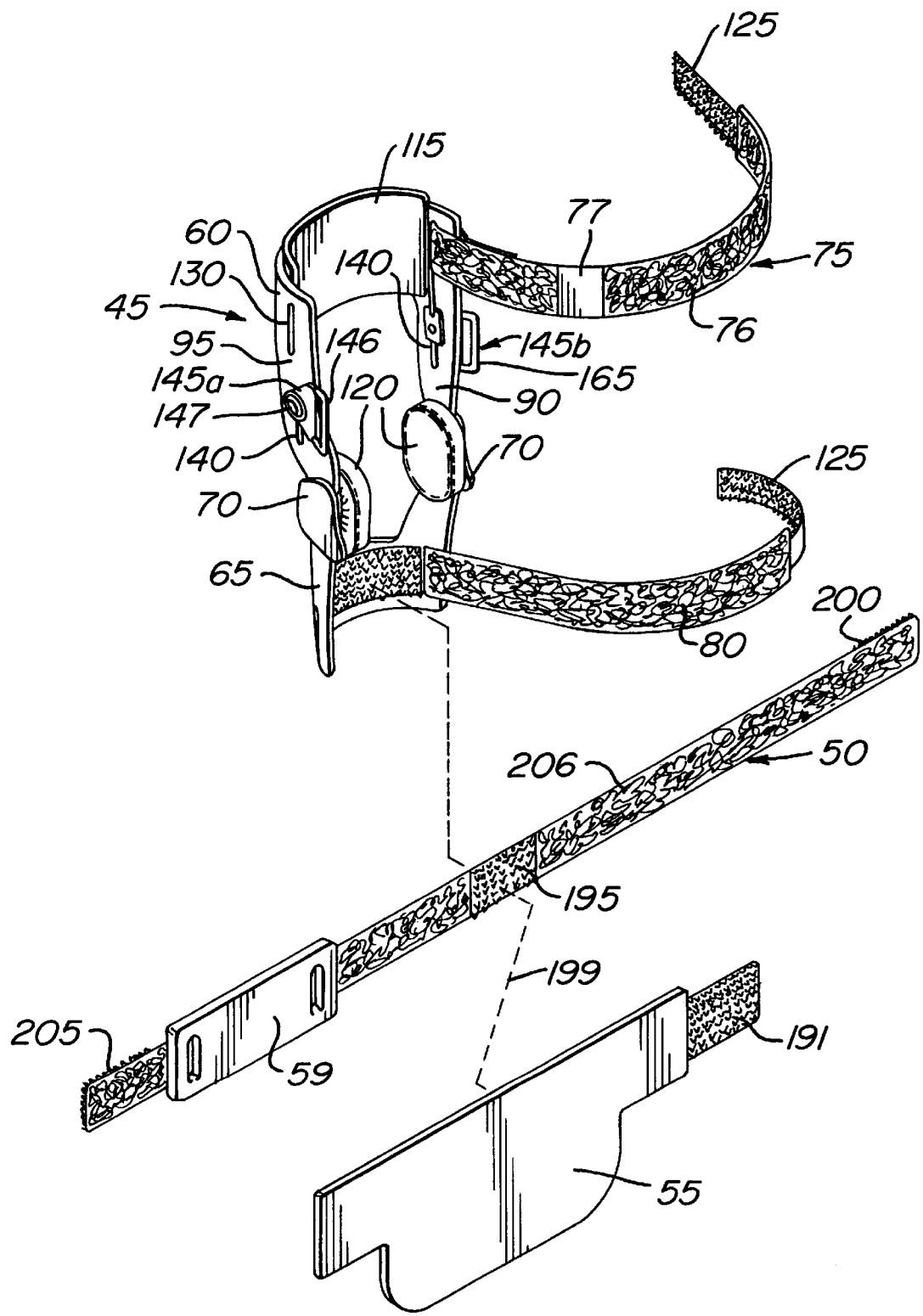
FIG. 7 is an exploded isometric view of a first embodiment of the present invention.

Referring now in greater detail to the various figures of the drawings wherein like reference numerals refer to like parts there is shown at 20 in FIGS. 1, 5 and 7 a first embodiment of the dynamic orthopedic knee brace assembly of the present invention. As shown in FIGS. 1 and 5, the knee brace assembly 20 is shown attached to a human left leg 25 (shown in phantom) having a thigh portion 30, a knee 35 and leg portion below the knee 40. The left leg 25 is chosen for convenience only and the brace assembly 20 can be affixed to either the right or left leg. Generally speaking, the knee brace assembly 20 functions to counteract anterior shifting of the tibia when the anterior cruciate ligament in the illustrated leg is missing or damaged. Such anterior shifting of the tibia occurs for a variety of reasons and often occurs when a person is engaging in physical activities that involve sudden turning to the right or to the left, sudden stopping, jumping, running backwards or other types of movement. Where the anterior cruciate ligament is missing or damaged, such anterior shifting of the tibia can also occur when a person simply extends his or her leg from a flexed position towards its fully straightened position (FIGS. 1 and 3). Referring now to FIG. 7, the knee brace assembly 20 of the present invention comprises three basic parts: a bracing component 45, a cross-strap 50 and a sleeve 55. The bracing component 45 comprises an upper or proximal cuff 60, which is engageable with a wearer's thigh, a distal cuff 65, which is engageable with the wearer's leg portion below the knee 40, and a pair of polycentric hinges 70 which pivotally join the cuffs 60 and 65 together. Straps, used for securing the cuffs to the wearer's leg, are shown generally at 75 and 80.

Referring now to FIGS. 1 and 7, the bracing component 45 is constructed to fit a wearer's leg as will become apparent hereinafter. The upper or proximal cuff 60, is formed to fit the anterior portion of the wearer's leg above the knee, and is essentially curvilinear in configuration and shaped to fit over the wearer's thigh 30. The proximal cuff 60 has medial and lateral depending portions 90 and 95, respectively, and a front arcuate portion 85 (FIG. 1). The proximal cuff 60 is open at the posterior portion so that it may be placed over the thigh 30 from the anterior or front. The distal cuff 65 is similar in construction to the proximal cuff in that it is curvilinearly shaped and formed to fit the anterior portion of the wearer's leg portion below the knee 40. It also includes a front arcuate portion 100, a medial depending portion 110 and a lateral depending portion 105.

The proximal and distal cuffs 60 and 65 and the polycentric hinges 70 are made of lightweight, high impact thermoplastic material which can be formed to fit the contours of the individual wearer's leg. The cuffs 60 and 65 may be fabricated from any suitable material, e.g., carbon fiber filament, carbon fiber filament and polymer composite, carbon/titanium composite, woven carbon fiber infused with acrylic resin. Preferably, the cuffs 60 and 65 are fabricated from a material that is water resistant and non-corrosive to enable the wearer to use the knee brace assembly in a full range of activities including working, walking, running, vigorous athletics and high-impact sports including freshwater and salt water sports.

Figure 6:
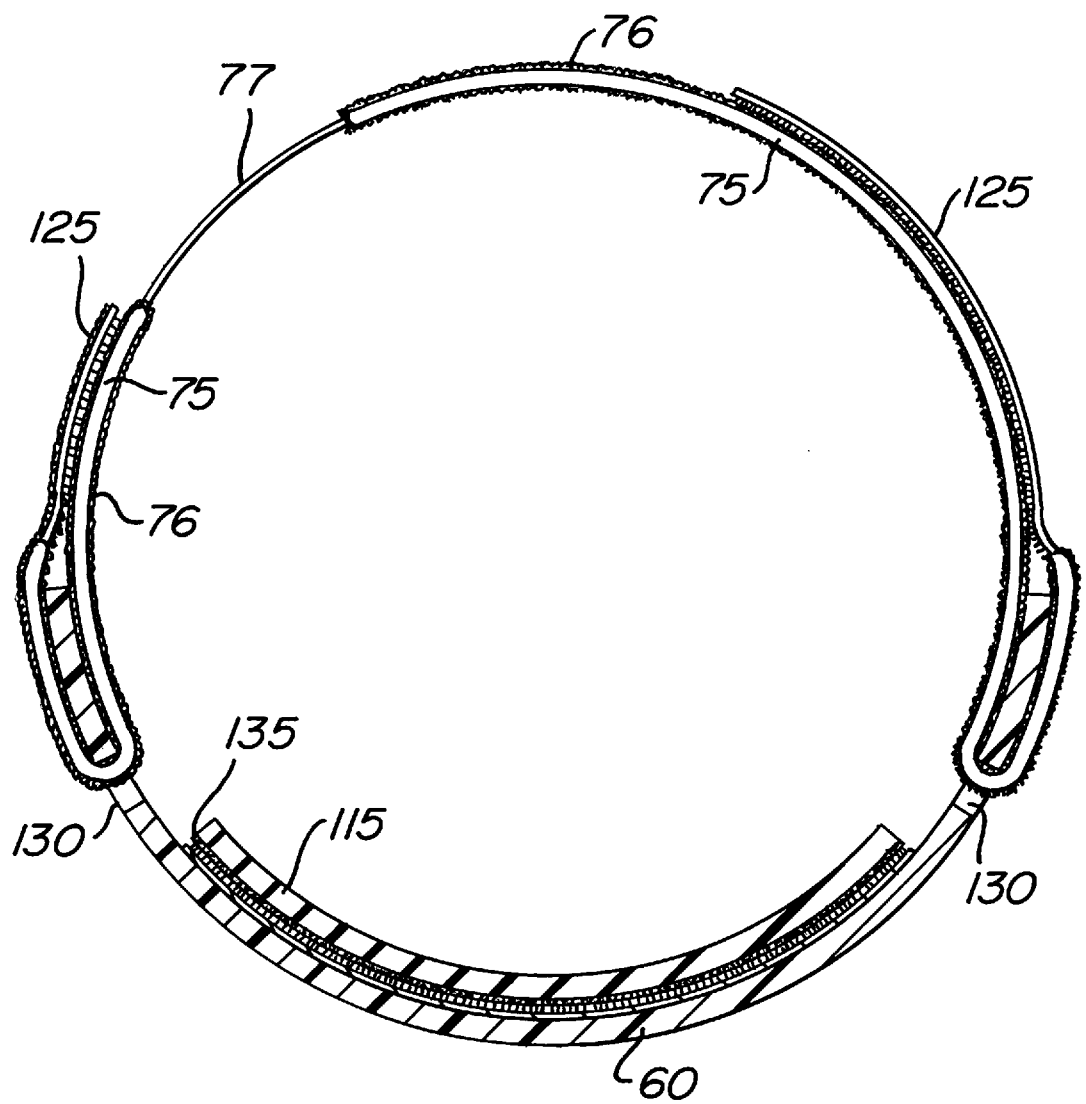
FIG. 6 is a sectional view taken along line 6—6 of FIG. 1.

Referring now to FIGS. 6 and 7, the proximal cuff 60 is padded on the inside surface by a durable non-allergenic foam pad 115. In FIG. 6, a top view of the knee brace assembly 20 is shown wherein the inside surface of the proximal cuff is provided with a VELCRO® hook patch 135 secured, e.g., glued, thereon that is arranged to be brought into engagement the plush exterior surface of the foam pad 115.

As shown in FIG. 7, the polycentric hinges 70 are also padded on the inside surface by a durable non-allergenic foam pad 120. The padded cuff and hinges are positioned to absorb anterior or frontal impacts, as well as lateral impacts to the outside of the leg and medial impacts to the inside of the leg.

Referring now to FIGS. 1, 6 and 7, the cuff strap 75 provides releasable securement of the proximal cuff 60 to the wearer's thigh 30. The cuff strap 75 may be formed of any suitable flexible material, e.g., nylon, and includes an elastic segment 77, VELCRO® loop segments 76 secured to the inner and outer surfaces thereof by any suitable means, e.g., sewing. The cuff strap 75 also includes VELCRO® hook segment 125 disposed at the free ends thereof. The free ends of the cuff strap 75 are slipped through and looped around elongated slots 130 located on opposite sides of the proximal cuff 60. Each free end of the cuff strap 75 is then folded back onto itself so that the hook segment 125 releasably engages the loop segment 76 thereby permitting the strap 75 to be tightened or loosened for comfort. The cuff strap 80 provides releasable securement of the distal cuff 65 to the wearer's leg below the knee 40 in a similar manner.

Referring now to FIGS. 1, 5 and 7, the medial and lateral depending portions 90 and 95 of the proximal cuff 60 each include a vertically oriented elongated slot 140. As best shown in FIG. 7, a strap guide assembly 145a is slidably mounted within the elongated slot 140 located on the lateral depending portion 95. Likewise, as best shown in FIG. 5, a strap guide assembly 145b is slidably mounted within the elongated slot 140 located on the medial depending portion 90 of the proximal cuff 60.

Figure 4:
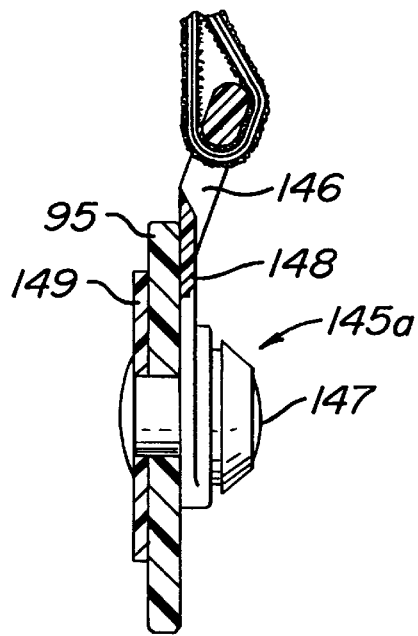
FIG. 4 is an enlarged sectional view taken along line 4—4 of FIG. 3.

Referring now to FIGS. 3 and 4, the strap guide assembly 145a shown therein includes a ring portion 146 trapped within a bracket portion 148. The bracket portion 148 is disposed over the outside surface of the lateral depending portion 95 of the proximal cuff 60. The strap guide assembly 145a also includes a flange portion 149 disposed on the inside surface of the lateral depending portion 95 of the cuff. The bracket 148 and flange 149 portions of the strap guide assembly 145a are held together and slidably mounted to the slot 140 by means of a rivet assembly 147 that enables the strap guide assembly 145a to slidably move within the slot 140 between two extremes: a distal extreme, as shown in FIG. 1 and a proximal extreme, as shown in FIG. 7.

Referring again to FIG. 3, an elastic band 160, e.g., a rubber band, is anchored at one of its ends to the flange 149 by any suitable means, e.g., tying. At its opposite end, the elastic band 160 is anchored to the inside surface of the lateral depending portion 95 of the proximal cuff 60 by any suitable means, e.g., rivet 166. In this manner, the elastic band 160 serves as a means for normally biasing the strap guide assembly 145a to the proximal extreme within the vertically oriented slot 140 as shown in FIG. 7, As best shown in FIG. 5, the strap guide assembly 145b is slidably mounted within the elongated slot 140 located on the medial depending portion 90 of the proximal cuff 60. The strap guide assembly 145b is similar in construction to the strap guide assembly 145a and includes a ring portion 165 trapped within a bracket portion 170 disposed over the outside surface of the medial depending portion 90 of the proximal cuff 60. The strap guide assembly 145b also includes a flange portion 175, the bracket and flange portions, 170 and 175, respectively, being held together and slidably mounted to the slot 140 by means of a rivet assembly 180 to enable the strap guide assembly 145b to slidably move between distal and proximal extremes. An elastic band 185, e.g., a rubber band, is anchored at one of its ends to the flange 175 by any suitable means, e.g., tying. At its opposite end, the elastic band 185 is anchored to the inside surface of the medial depending portion 90 of the proximal cuff 60 by any suitable means, e.g., rivet 190. In this manner, the elastic band 185 serves as a means to normally bias the strap guide assembly 145b to the proximal extreme within the vertically oriented slot 140 as shown in FIG. 5.

Referring now to FIGS. 1, 5 and 7, the prosthetic sleeve 55 is provided to assist in the attachment of the cross strap 50 and may be constructed of any suitable material, e.g., one-eighth inch thick neoprene having a brushed nylon outer surface and a smooth neoprene inner surface. The sleeve 55 is shown as being arranged to be wrapped around and secure to the wearer's leg portion just below the knee 40. An alternative sleeve, such as a full patella support sleeve which wraps around and secures to the wearer's thigh and calf, both above and below the wearer's knee could be utilized in substitution for the sleeve 55 in accordance with this invention. As best shown in FIG. 7, the sleeve 55 is provided with a laterally extending attachment strap 191 on which a VELCRO® hook segment is disposed. As best shown in FIG. 5, once the sleeve 55 is wrapped around the wearer's calf just below the knee 35, the hook segment on the attachment strap 191 releasably engages the plush outer surface of the sleeve 55 thereby permitting the sleeve 55 to be tightened or loosened for comfort.

Figure 2:
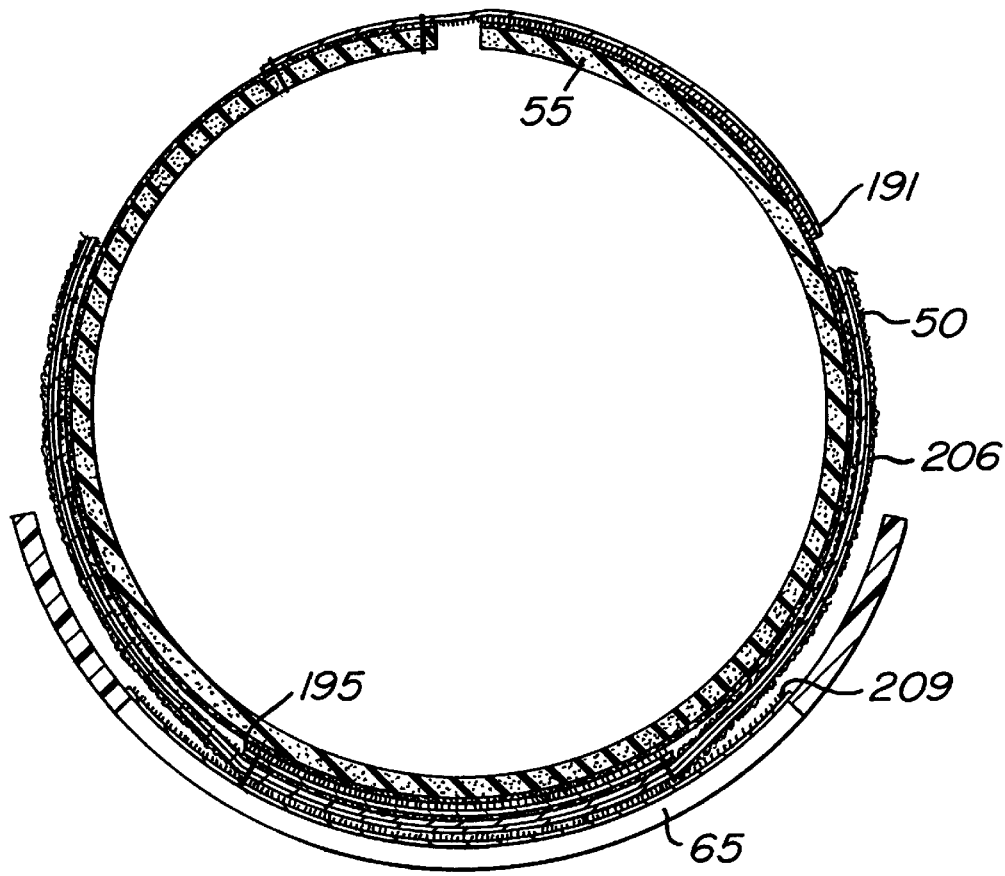
FIG. 2 is an enlarged sectional view taken along line 2—2 of FIG. 1.

Referring now to FIG. 7, the cross-strap 50 is formed of a non-elastic flexible web using any suitable material, e.g., nylon, and comprises an interior surface (best shown in FIGS. 2 and 7), an exterior surface (best shown in FIG. 2) and free ends to which VELCRO® hook patches 200 and 205 are secured. As best shown in FIGS. 2 and 7, VELCRO® loop segments 206 are secured to both the interior and exterior surfaces of the cross-strap 50 by any suitable means, e.g., sewing. Positioned on the interior surface of the cross-strap 50 approximately midway along the length thereof is a VELCRO® hook patch 195 arranged for releasable securement with the plush exterior surface of the sleeve 55 at a position on the sleeve 55 that lies over the wearer's tibia just below the wearer's knee 35. The positioning of the hook patch 195 on the outer surface of the sleeve 55 is best illustrated in FIG. 1 and by the dotted line 199 in FIG. 7. The cross-strap 50 is also provided with a pad 59 slidably mounted thereon to be positioned behind the wearer's knee when the cross-strap is secured to the wearer's leg in the manner described below.

Referring now to FIGS. 1 and 5, once the hook patch 195 cross strap 50 is releasably secured to the sleeve 55 in the manner described above, the proximal and distal cuffs 60 and 65 of the bracing component 45 are releasably secured to the wearer's thigh 30 and leg portion below the knee 40 by attachment with straps 75 and 80. As best shown in FIG. 2, a VELCRO® hook patch 209 is secured, e.g., glued, to the inside surface of the distal cuff 65 and is provided to engage with the plush exterior surface of the sleeve 55 thus providing an added means for securing the distal cuff 65 to the wearer's leg portion below the knee 40.

Thereafter, the free ends of the cross-strap 50 are crossed behind the wearer's knee 35 and slipped through and looped around the ring portions 146 and 165 of the pivotally mounted strap guide assemblies 145a and 145b. Each free end of the cross-strap 50 is then folded back onto itself so that the hook patches 200 and 205 releasably engage the loop segments 206 of the cross-strap 50 thereby permitting the cross-strap 50 to be tightened or loosened for comfort. The slidable pad 59 may be positioned behind the wearer's knee to suit the user's comfort. In accordance with this invention, when releasably securing the free ends of the cross-strap to the strap guide assemblies 145a and 145b, the wearer must maintain his or her knee in approximately thirty degrees of flexion. Moreover, the cross-strap must be applied to fit snugly around the wearer's knee but not so tightly as to be uncomfortable.

During use of the knee brace assembly 20, when the wearer's leg is fully flexed, the quadriceps muscle exerts only a relatively slight anterior displacement force on the tibia. This displacement force increases significantly as the wearer extends his or her leg closer and closer toward the fully extended position. It can be readily seen that when wearing the brace 20, as the wearer begins to extend his or her leg 25 towards full extension, the cross-strap 50 tightens geometrically around the wearer's knee 35 above and below the joint line and also applies posteriorly directed pressure to the anterior portion of the wearer's tibia just below the knee. The posteriorly directed pressure exerted against the tibia by the cross-strap 50 restrains anterior translation of the tibia.

At this juncture, it is important to point out that anterior tibial translation can result from a number of causes other than displacement forces created by the quadriceps muscle.

For example, anterior tibial translation can result from force exerted against the tibia when the wearer is engaged in physical activity that involves sudden turning to the left or right, sudden stopping, jumping and running backwards. The posteriorly directed pressure exerted against the tibia by the cross-strap 50 will restrain anterior translation of the tibia during such physical activity.

At the same time, the cross-strap 50 applies a tensile force upon the strap guide assemblies 145a and 145b urging them to move from their normally biased proximal extreme to their distal extreme. As the strap guide assemblies move towards the distal extreme, the elastic bands 160, 185 will stretch and exert a counteractive tensile force upon the strap guide assemblies resistive to their distal movement. The movement of the strap guide assemblies enables the wearer to straighten his or her leg into full extension while applying increasing amounts of pressure to the wearer's tibia just below the knee.

Figure 8:
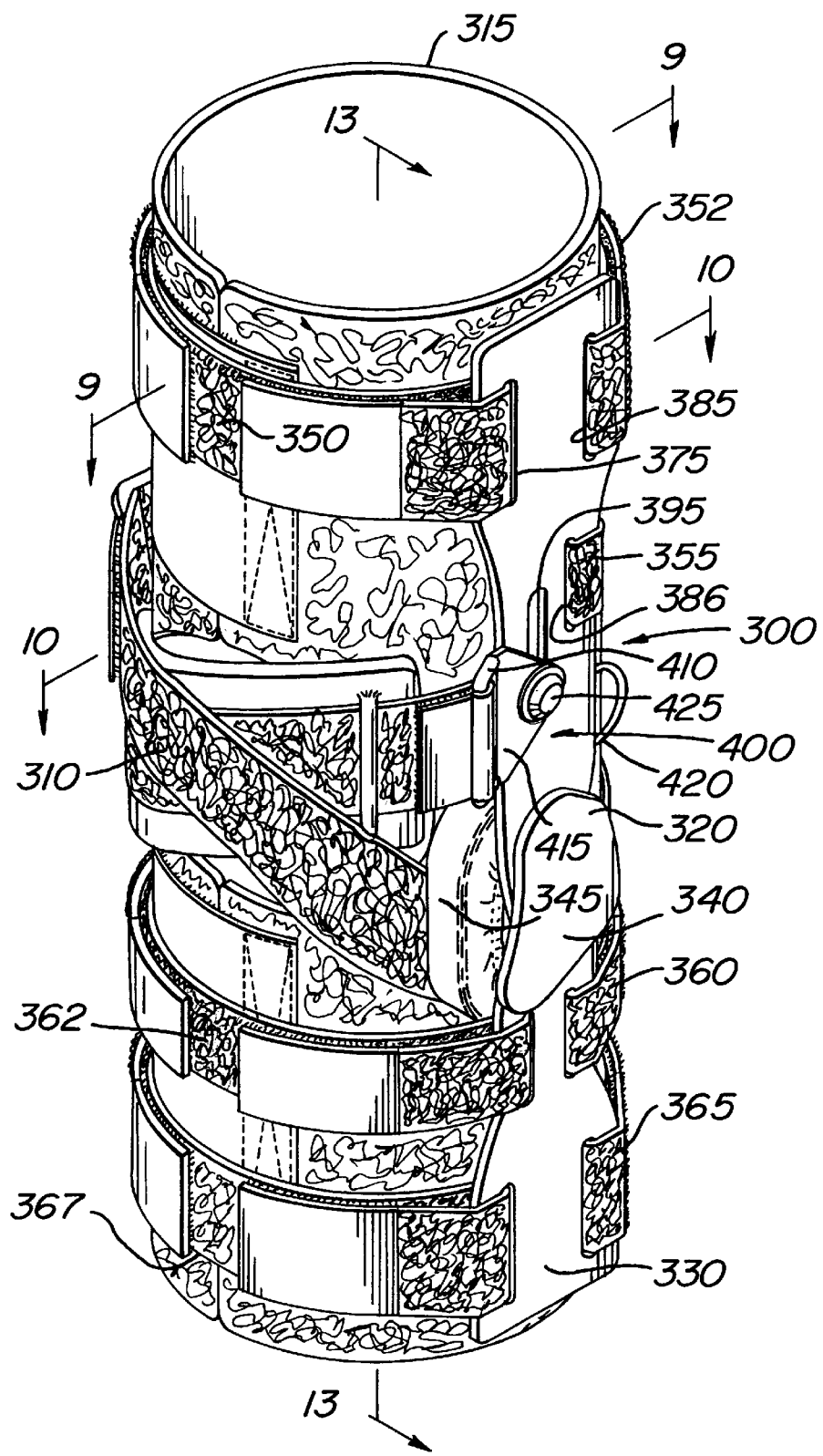
FIG. 8 is an isometric view of a second embodiment of the present invention.
Figure 14:
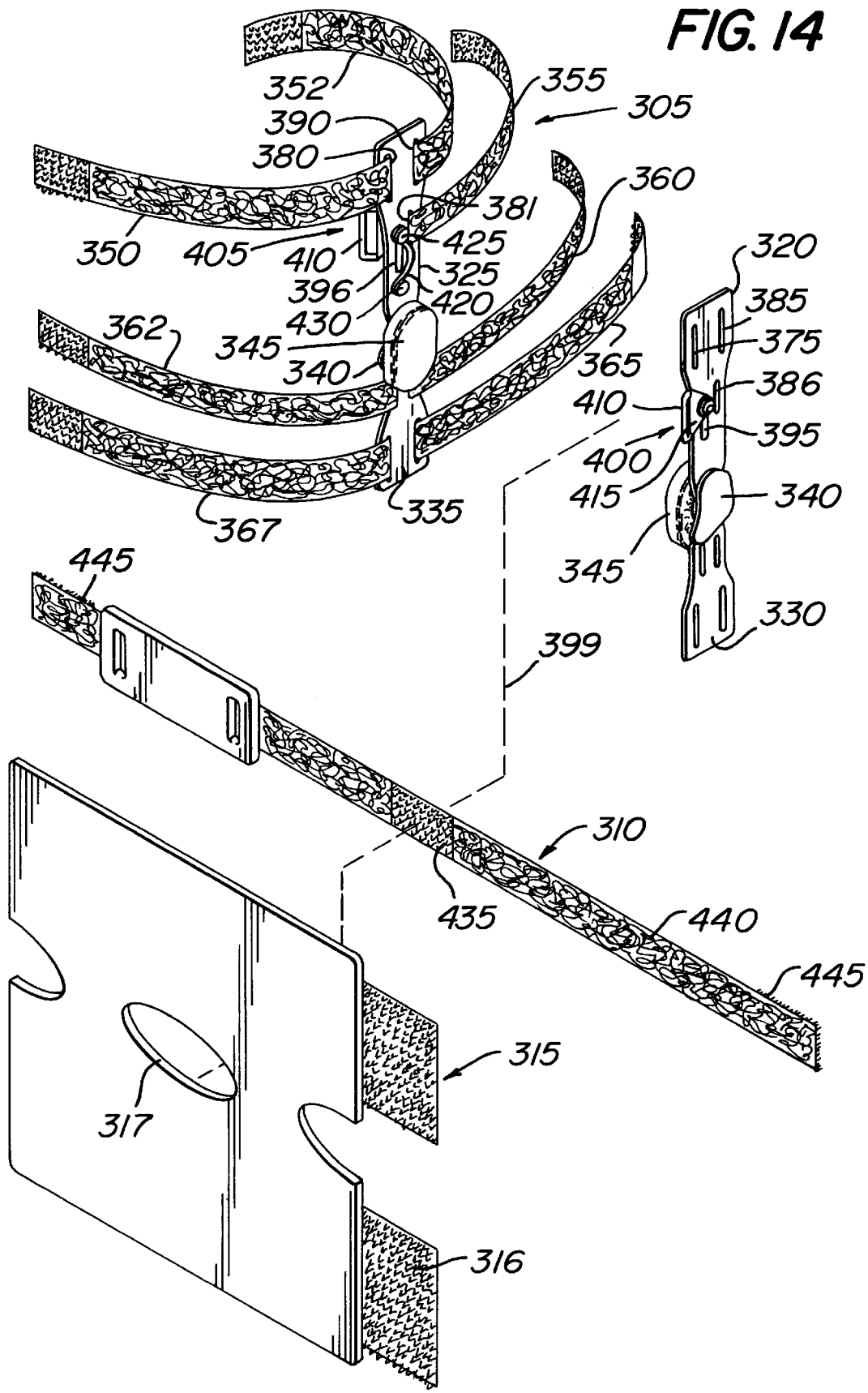

Referring now to FIGS. 8 and 14, there is shown at 300 a second embodiment of the dynamic orthopedic knee brace assembly of the present invention. As best shown in FIG. 14, the knee brace assembly 300 shown therein comprises three basic parts: a bracing component 305, a cross-strap 310 and a sleeve 315. The knee brace assembly 300 functions to counteract anterior shifting of the tibia that can occur during physical activities that involve sudden turning to the right or left, sudden stopping, jumping or running backwards when the anterior cruciate ligament in the illustrated leg is missing or damaged.

As best shown in FIGS. 8 and 14, the bracing component 305 comprises a pair of elongated rigid thigh support members 320 and 325 extending along medial and lateral sides of the thigh, respectively, and a pair of elongated rigid lower leg support members 330 and 335 extending along the medial and lateral sides of the wearer's leg portion below the knee, respectively. The inner ends of the thigh and lower leg support pairs are pivotally interconnected by means of a pair of polycentric hinges 340. The thigh support members 320, 325, lower leg support members 330, 335 and polycentric hinges 340 are made of any suitable lightweight material, e.g., carbon fiber filament, thermosensitive carbon composite materials. Preferably, these components are fabricated from a material that is water resistant and non-corrosive to enable the wearer to use the knee brace assembly in a full range of activities including working, walking, and vigorous athletics. The polycentric hinges 340 are padded on the inside surface by a durable non-allergenic foam pad 345.

Figure 9:
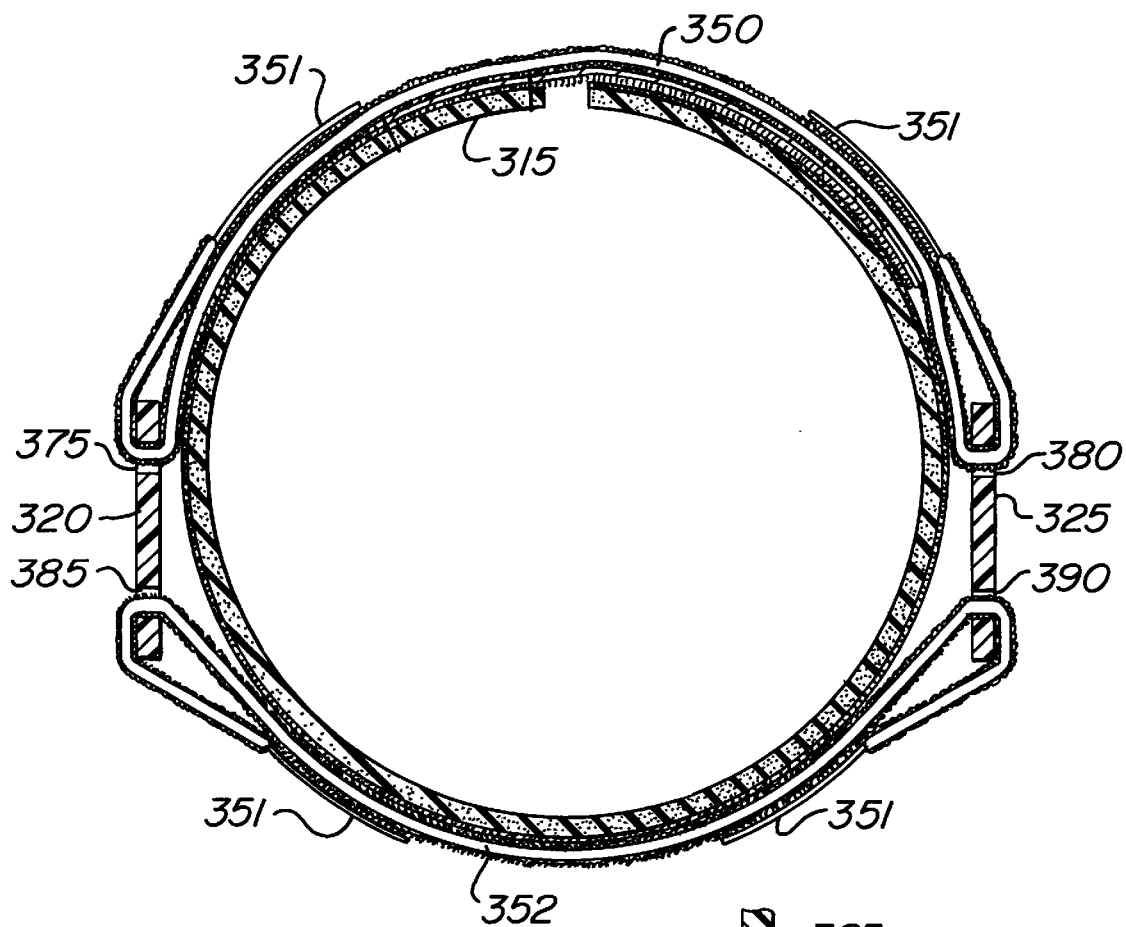
FIG. 9 is an enlarged sectional view taken along line 9—9 of FIG. 8.
Figure 12:
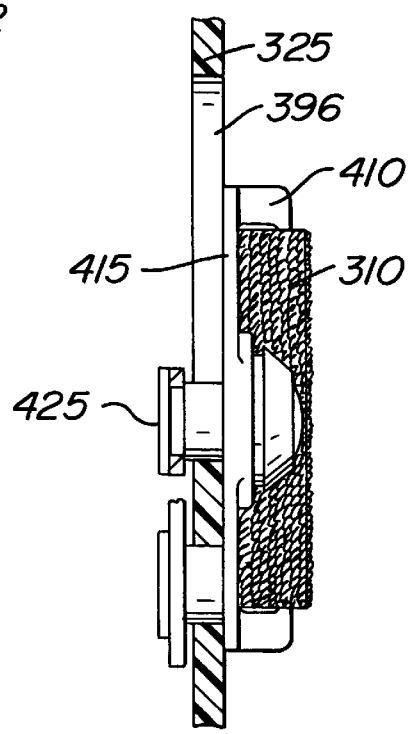
FIG. 12 is an enlarged sectional view taken along line 12—12 of FIG. 10.

As best shown in FIGS. 8 and 14, the support members are releasably secured to the wearer's leg (not shown) above and below the knee by means of straps shown generally at 350, 352, 355, 360, 362, 365 and 367. Referring now to FIG. 9, a top view of the knee brace assembly 300 is shown therein illustrating the manner in which the straps 350 and 352 releasably secure the rigid thigh support members 320 and 325 to the wearer's thigh. The straps 350 and 352, shown therein, each include a VELCRO® hook segment 351 disposed at each end thereof. One end of the strap 350 is slipped through and looped around an elongated slot 375 located in the thigh support member 320 while the other end of the strap 350 is slipped through and looped around an elongated slot 380 located in the thigh support member 325. One end of the strap 352 is slipped through and looped around an elongated slot 385 located in the lateral thigh support member 320 while the other end of the strap 352 is slipped through and looped around an elongated slot 390 located in the medial thigh support member 325. Each end of the straps 350 and 352 is then folded back onto itself so that the hook segments 351 releasably engage VELCRO® loop segments secured, e.g., sewn, to the outer surface of the straps 350 and 352 thereby permitting the straps 350 and 352 to be tightened or loosened for comfort. Referring now to FIGS. 8 and 14, the strap 355 slips through and loops around elongated slots 381 and 386 and releasably engages to itself in the manner in which strap 350 and 352 releasably engage.

Referring now to FIG. 8, straps 355, 360, 362, 365 and 367 releasably secure the rigid lower leg support members 330 and 335 to the wearer's leg portion below the knee in a manner similar to that described above in connection with releasable attachment of the rigid thigh support members to the wearer's thigh using straps 350, 352 and 355.

Figure 10:
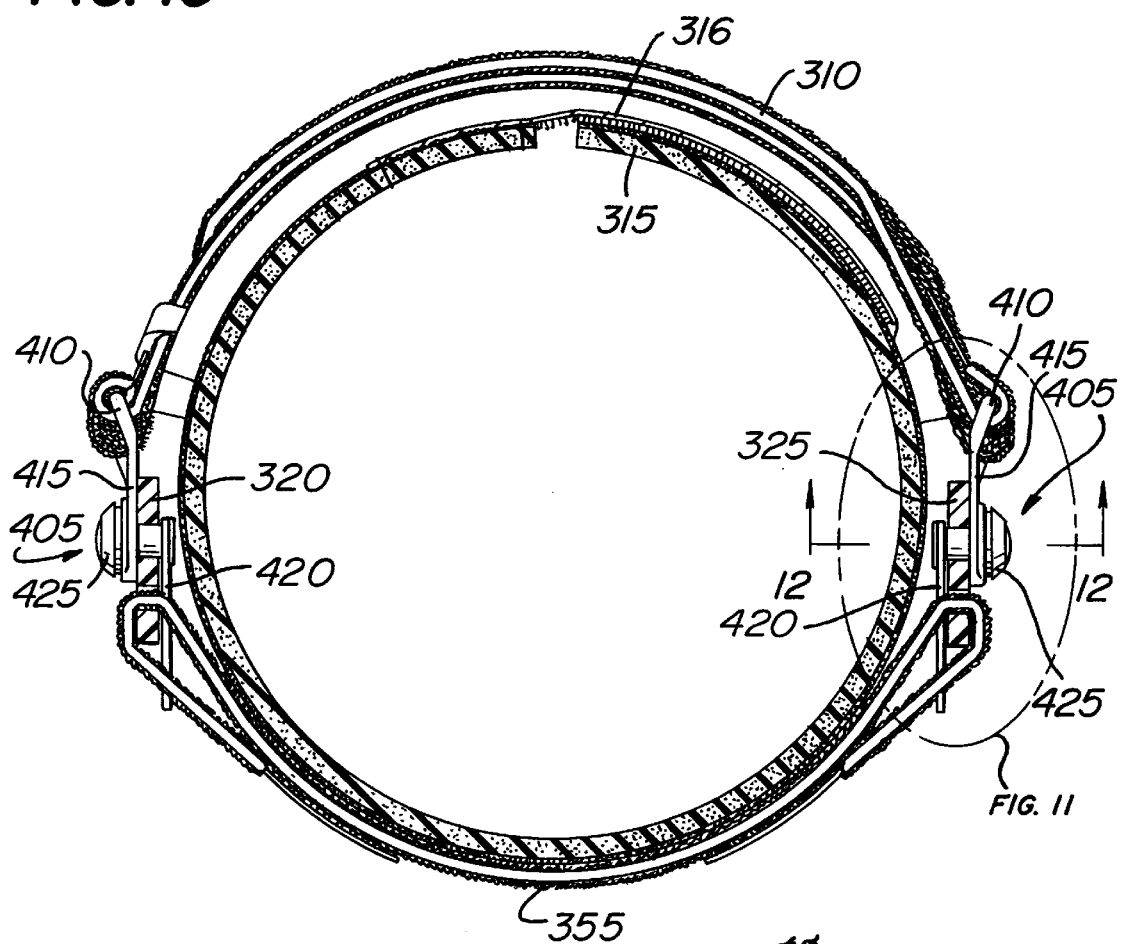
FIG. 10 is an enlarged sectional view taken along line 10—10 of FIG. 8.
Figure 11:
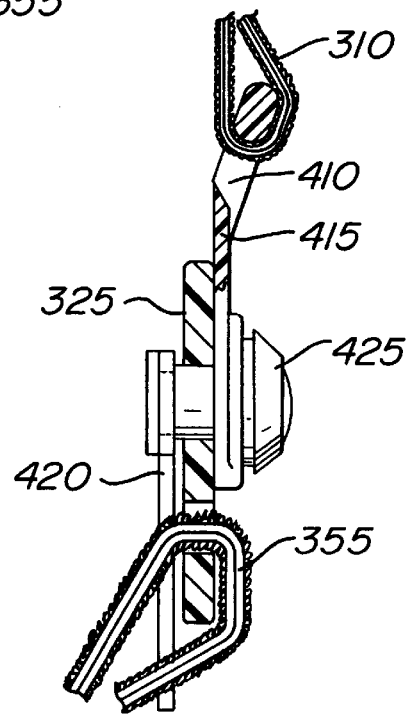
FIG. 11 is an enlarged view of an area shown in FIG. 10 encircled by a line labeled FIG. 11.

Referring now to FIGS. 8 and 14, the rigid thigh support member 320 includes a vertically oriented elongated slot 395 in which a strap guide assembly 400 is slidably mounted. Similarly, the rigid thigh support member 325 includes a vertically oriented elongated slot 396 in which a strap guide assembly 405 is slidably mounted. The strap guide assemblies 400 and 405 each include a ring portion 410 trapped within a bracket portion 415. As best shown in FIGS. 10 and 11, the bracket portion 415 of each strap guide assembly 400 and 405 is disposed over the outside surface of the thigh support members 320 and 325. As best shown in FIGS. 8 and 13, each strap guide assembly 400 and 405 also includes a leaf spring 420 disposed on the inside surface of the thigh support members 320 and 325. As best shown in FIGS. 11 and 14, the bracket portion 415 and one end of the leaf spring portion 420 of the strap guide assemblies 400 and 405 are secured together and mounted on opposite sides of the elongated slots 395 and 396 by means of a rivet assembly 425 that enables the strap guide assemblies 400 and 405 to slidably move within the slots 395 and 396 between two extremes: a distal extreme, as shown in FIGS. 8 and 13, and a proximal extreme (not shown).

Referring now to FIGS. 13 and 14, as previously mentioned, one end of the leaf spring 420 is secured to the strap guide assemblies 400 and 405 by means of a rivet 425. At its other end, the leaf springs 420 is anchored to the inside surface of the rigid thigh support members 320 and 325 by means of a rivet assembly 430. In this manner, the leaf spring 420 serves as a means for normally biasing the strap guide assemblies 400 and 405 to the proximal extreme within the vertically oriented slots 395 and 396, respectively. At this juncture it is important to point out that rather than a leaf spring, alternative means could be employed for biasing the strap guide assemblies towards the proximal extreme, e.g., a coiled spring, an elastic band, a rubber band, etc.

Referring now to FIGS. 8 and 14, the prosthetic sleeve 315 is provided to assist in the attachment of the cross-strap 310 and may be constructed of any suitable material, e.g., one-eighth inch thick neoprene having a plush outer surface and a smooth neoprene inner surface. The sleeve 315 shown is a full patella support sleeve which wraps around and secures to the wearer's thigh and calf above and below the wearer's knee. As best shown in FIG. 14, the sleeve 315 is provided with a laterally extending attachment strap 316 on which a VELCRO® hook segment is disposed. The sleeve 315 also provides a patella opening 317 through which the knee can protrude when the sleeve 315 is worn. Once the sleeve 315 is wrapped around the wearer's leg, the attachment strap 316 releasably engages the plush outer surface of the sleeve 315 to be tightened or loosened for comfort.

The cross-strap 310 is formed of a non-elastic flexible web using any suitable material, e.g., nylon, and comprises free ends, an interior surface, shown in FIG. 14 and an exterior surface, hidden from view in FIG. 14. The interior surface comprises VELCRO® loop segments 440 secured thereto by any suitable means, e.g., sewing, and a centrally located VELCRO® hook patch 435 also secured thereto by any suitable means, e.g., sewing. The hook patch 435 is arranged for releasable securement with the plush exterior surface of the sleeve 315 just below the patella opening 317 of the sleeve 315. This position, as best illustrated by the dotted line 399 in FIG. 14, corresponds with the wearer's tibia. The exterior surface of the cross-strap 310 comprises VELCRO® hook patches 445 at the free ends thereof and a VELCRO® loop segment (not shown) extending therebetween. The cross-strap 310 is also provided with a pad 359 slidably mounted thereon to be positioned behind the wearer's knee when the cross-strap 310 is releasably secured to the wearer's leg.

Once the cross-strap 310 is releasably secured to the sleeve 315 at the location described above and illustrated in FIG. 14, i.e., just below the patella opening 317, the bracing component 305 is releasably secured to the wearer's thigh and leg portion below the knee using straps 350, 352, 355, 360, 362, 365 and 367. Thereafter, the free ends of the cross-strap 310 are crossed behind the wearer's knee and slipped through and looped around the ring portions 410 of the pivotally mounted strap guide assemblies 400 and 405. Each free end of the cross-strap 310 is then folded back onto itself so that the hook patches 445 releasably engage the loop segment secured thereby permitting the cross-strap 310 to be tightened or loosened for comfort.

During use of the knee brace assembly 300, when the wearer's leg is fully flexed, the quadriceps muscle exerts only a relatively slight anterior displacement force on the tibia. This displacement force increases significantly as the wearer extends his or her leg closer and closer toward the fully extended position. It can be readily seen that when wearing the brace 300, as the wearer begins to extend his or her leg towards full extension, the cross-strap 310 tightens geometrically around the wearer's knee above and below the joint line and also applies posteriorly directed pressure to the anterior portion of the wearer's tibia just below the knee. This posteriorly directed pressure exerted against the tibia by the cross-strap 310 restrains anterior translation of the tibia.

At this juncture, it is important to point out that anterior tibial translation can result from a number of causes other than displacement forces created by the quadriceps muscle. For example, anterior tibial translation can result from force exerted against the tibia when the wearer is engaged in physical activity that involves sudden turning to the left or right, sudden stopping, jumping and running backwards. The posteriorly directed pressure exerted against the tibia by the cross-strap 310 will restrain anterior translation of the tibia during such physical activity.

At the same time, the cross-strap 310 applies a tensile force upon the strap guide assemblies 400 and 405 urging them to move from their normally biased proximal extreme to their distal extreme. As best shown in FIG. 13, as the strap guide assemblies move towards the distal extreme, the leaf springs 420 will compress and exert a counteractive tensile force upon the strap guide assemblies resistive to their distal movement. The movement of the strap guide assemblies enables the wearer to straighten his or her leg into full extension while exerting additional counteractive force to prevent anterior translation of the tibia.

I claim:

1. A knee brace assembly for restricting anterior translation of a wearer's tibia, the wearer also having a leg including a thigh, a knee and a leg portion below the knee, said knee brace assembly comprising:
   a. first means for engaging the wearer's thigh, said first means comprising a lateral portion positioned over the lateral side of the wearer's thigh and a medial portion positioned over the medial side of the wearer's thigh, said lateral and medial portions each having a slot extending there along;
   b. second means for engaging the wearer's leg portion below the knee;
   c. hinging means linked to said first and second means to permit pivotal movement of said first means relative to said second means;
   d. strap guiding means slidably mounted within each of said slots, said strap guiding means being arranged to slide between a proximal extreme when the wearer's leg is in flexion towards a distal extreme as the wearer extends his or her leg;
   e. biasing means resiliently biasing said moveable strap guides towards said proximal extreme; and,
   f. a cross-strap provided for engagement with the wearer's leg, said cross-strap comprising free ends and a length therebetween, a portion of said length comprising tibial pressure application means, said cross-strap being attachable over the wearer's leg with said tibial pressure application means located over the wearer's tibia, said cross-strap wrapping behind the wearer's knee in a crisscross manner, the free ends of said cross-strap being attachable to said strap guiding means and in response to extension of the wearer's leg said cross-strap tightening geometrically around the wearer's knee and pulling said strap guiding means from said proximal extreme towards said distal extreme thus enabling said tibial pressure application means to provide resistance to the anterior movement of the tibia.

2. The knee brace assembly of claim 1 wherein said first means comprises a proximal cuff engageable with the wearer's thigh and wherein said second means comprises a distal cuff engageable with the wearer's leg portion below the knee.

3. The knee brace assembly of claim 2 wherein said proximal cuff additionally comprises an arcuate portion for engagement with the anterior portion of the wearer's thigh and said distal cuff additionally comprises an arcuate portion for engagement with the anterior portion of the wearer's leg below the knee.

4. The knee brace assembly of claim 2 wherein said medial and lateral portions of said proximal cuff and said medial and lateral portions of said distal cuff are pivotally connected to said hinging means.

5. The knee brace assembly of claim 2 wherein said biasing means comprises an elastic band anchored at one end to said proximal cuff, said elastic band being connected at its opposite end to said strap guiding means.

6. The knee brace assembly of claim 2 wherein said biasing means comprises a spring anchored at one end to said proximal cuff, said spring being connected at its opposite end to said strap guiding means.

7. The knee brace assembly of claim 6 wherein said spring is a leaf spring.

8. The knee brace assembly of claim 2 wherein said proximal cuff additionally comprises a longitudinal axis, said slots extending parallel to said longitudinal axis.

9. The knee brace assembly of claim 2 wherein said proximal and distal cuffs are formed of lightweight, high-impact thermoplastic material.

10. The knee brace assembly of claim 2 wherein said proximal and distal cuffs are formed of a carbon fiber filament material.

11. The knee brace assembly of claim 2 additionally comprising a sleeve encircling the wearer's leg below the knee, said cross-strap being releasably attachable over said sleeve.

12. The knee brace assembly of claim 11 wherein said distal cuff is engageable with the wearer's leg over said suspension sleeve.

13. The knee brace assembly of claim 2 additionally comprising adjustably tightenable first strap means for engaging said proximal cuff to the wearer's thigh and adjustably tightenable second strap means for engaging said distal cuff to the wearer's leg portion below the knee.

14. The knee brace assembly of claim 13 wherein each of said first and second strap means includes an elastic segment.

15. The knee brace assembly of claim 1 wherein each of said medial and lateral portions comprises a rigid thigh support member engageable with the wearer's thigh and wherein said second means comprises a pair of rigid calf support members engageable with the wearer's leg portion below the knee.

16. The knee brace assembly of claim 1 wherein said cross-strap is non-elastic and adjustably tightenable to selectively vary the magnitude of said force counteractive to abnormal anterior movement of the tibia.

17. The knee brace assembly of claim 1 wherein said hinging means comprises a pair of hinges positioned over the medial and lateral sides of the wearer's knee.

18. The knee brace assembly of claim 17 wherein said proximal and distal cuffs and said hinges are lined with non-allergenic foam padding for direct engagement with the wearer's skin.

19. The knee brace assembly of claim 17 wherein said hinges are polycentric hinges.

20. The knee brace assembly of claim 1 wherein said strap guide means are pivotable.

21. The knee brace assembly of claim 1 wherein said cross-strap is adjustable.

* * * * *